(12) United States Patent
Rafiee et al.

(10) Patent No.: US 12,133,962 B2
(45) Date of Patent: Nov. 5, 2024

(54) CATHETERS AND MANIPULATORS WITH ARTICULABLE ENDS

(71) Applicants: Transmural Systems LLC, Andover, MA (US); The UNITED STATES OF AMERICA, as represented by the Secretary, Dept. of Health and Human Srvcs., Bethesda, MD (US)

(72) Inventors: Nasser Rafiee, Andover, MA (US); Robert J. Lederman, Bethesda, MD (US); Toby Rogers, Bethesda, MD (US); Dursun Korel Yildirim, Bethesda, MD (US); Mai Le Diep, Andover, MA (US); Koosha Rafiee, Andover, MA (US)

(73) Assignees: Transmural Systems LLC, Andover, MA (US); United States Department of Health and Human Services, Bethesda, MD (US)

( * ) Notice: Subject to any disclaimer, the term of this patent is extended or adjusted under 35 U.S.C. 154(b) by 807 days.

(21) Appl. No.: 16/563,925

(22) Filed: Sep. 8, 2019

(65) Prior Publication Data
US 2020/0001053 A1   Jan. 2, 2020

Related U.S. Application Data

(63) Continuation-in-part of application No. PCT/US2018/048177, filed on Aug. 27, 2018.
(Continued)

(51) Int. Cl.
*A61M 25/09* (2006.01)
*A61B 18/12* (2006.01)
(Continued)

(52) U.S. Cl.
CPC ....... *A61M 25/09025* (2013.01); *A61B 18/12* (2013.01); *A61M 25/0105* (2013.01);
(Continued)

(58) Field of Classification Search
CPC .......... A61B 18/12; A61B 2018/00077; A61B 2018/00184; A61B 2018/00279;
(Continued)

(56) References Cited

U.S. PATENT DOCUMENTS

| 4,493,320 A | 1/1985 | Treat |
| 5,417,697 A | 5/1995 | Wilk et al. |

(Continued)

FOREIGN PATENT DOCUMENTS

| DE | 10037660 A1 | 2/2002 |
| DE | 202010016945 U1 | 3/2011 |

(Continued)

OTHER PUBLICATIONS

Written Opinion of the International Searching Authority for International Application No. PCT/US2018/048177 mailed Nov. 19, 2018.
(Continued)

*Primary Examiner* — Joseph A Stoklosa
*Assistant Examiner* — Annie L Shoulders
(74) *Attorney, Agent, or Firm* — DeWitt LLP; Brian R. Pollack, Esq.

(57) ABSTRACT

The disclosure provides various embodiments of catheters having articulable ends that can be used for various procedures. Embodiments of methods are also provided that can be performed with catheters in accordance with the present disclosure.

15 Claims, 10 Drawing Sheets

Related U.S. Application Data

(60) Provisional application No. 62/550,347, filed on Aug. 25, 2017, provisional application No. 62/567,203, filed on Oct. 2, 2017, provisional application No. 62/663,518, filed on Apr. 27, 2018, provisional application No. 62/688,378, filed on Jun. 21, 2018, provisional application No. 62/712,194, filed on Jul. 30, 2018, provisional application No. 62/728,413, filed on Sep. 7, 2018.

(51) Int. Cl.
*A61B 18/14* (2006.01)
*A61M 25/01* (2006.01)
*A61B 18/00* (2006.01)

(52) U.S. Cl.
CPC .............. *A61B 2018/00077* (2013.01); *A61B 2018/00184* (2013.01); *A61B 2018/00279* (2013.01); *A61B 2018/00369* (2013.01); *A61B 2018/00601* (2013.01); *A61B 2018/1213* (2013.01); *A61B 2018/126* (2013.01); *A61B 2018/141* (2013.01); *A61B 2018/1417* (2013.01); *A61B 2018/1432* (2013.01); *A61M 2025/09133* (2013.01); *A61M 2025/09175* (2013.01)

(58) Field of Classification Search
CPC .......... A61B 2018/00369; A61B 2018/00601; A61B 2018/1213; A61B 2018/126; A61B 2018/141; A61B 2018/1417; A61B 2018/1432; A61M 2025/09133; A61M 2025/09175; A61M 25/09025; A61M 25/0105

See application file for complete search history.

(56) References Cited

U.S. PATENT DOCUMENTS

| | | |
|---|---|---|
| 5,599,300 A | 2/1997 | Weaver et al. |
| 5,807,279 A | 9/1998 | Viera |
| 6,017,340 A | 1/2000 | Cassidy et al. |
| 6,050,995 A | 4/2000 | Durgin |
| 6,501,992 B1 | 12/2002 | Belden et al. |
| 6,517,551 B1 | 2/2003 | Driskill |
| 6,533,782 B2 | 3/2003 | Howell et al. |
| 6,582,425 B2 | 6/2003 | Simpson |
| 6,695,836 B1 | 2/2004 | DeMello et al. |
| 7,160,295 B1 | 1/2007 | Garito et al. |
| 7,303,798 B2 | 12/2007 | Bavaro et al. |
| 7,455,646 B2 | 11/2008 | Richardson et al. |
| 8,827,948 B2 | 9/2014 | Romo et al. |
| 9,282,993 B1 | 3/2016 | Cohen et al. |
| 9,572,666 B2 | 2/2017 | Basude et al. |
| 9,833,272 B2 | 12/2017 | Sweeney |
| 9,980,716 B2 | 5/2018 | Harris et al. |
| 10,143,481 B2 | 12/2018 | Golan |
| 2002/0173811 A1* | 11/2002 | Tu .................... A61B 17/22031 606/159 |
| 2003/0088195 A1 | 5/2003 | Vardi et al. |
| 2004/0267161 A1 | 12/2004 | Osborne et al. |
| 2005/0171532 A1 | 8/2005 | Ciarocca |
| 2007/0293857 A1 | 12/2007 | Blind et al. |
| 2008/0228209 A1 | 9/2008 | DeMello et al. |
| 2009/0005637 A1 | 1/2009 | Chin et al. |
| 2010/0022823 A1* | 1/2010 | Goldfarb ............ A61B 17/0401 600/37 |
| 2012/0123328 A1 | 5/2012 | Williams |
| 2013/0304200 A1* | 11/2013 | McLean ................ A61F 2/2445 623/2.18 |
| 2014/0276605 A1 | 9/2014 | Tejani et al. |
| 2017/0007277 A1 | 1/2017 | Drapeau et al. |
| 2018/0008268 A1 | 1/2018 | Khairkhahan |
| 2018/0028215 A1* | 2/2018 | Cohen ............ A61B 17/320016 |
| 2019/0029790 A1* | 1/2019 | Bak-Boychuk ......... A61F 2/013 |
| 2019/0298521 A1 | 3/2019 | Rafiee et al. |
| 2019/0175199 A1 | 6/2019 | Girdhar et al. |
| 2020/0383717 A1 | 12/2020 | Lederman et al. |

FOREIGN PATENT DOCUMENTS

| | | |
|---|---|---|
| EP | 3175813 B1 | 1/2020 |
| RU | 2152757 C1 | 7/2000 |
| WO | 2018009718 A1 | 1/2018 |
| WO | 2019/040943 A1 | 2/2019 |
| WO | 2019164806 A1 | 8/2019 |
| WO | 2021007324 A1 | 1/2021 |
| WO | 2021072331 A1 | 4/2021 |
| WO | 2022066621 A1 | 3/2022 |

OTHER PUBLICATIONS

International Search Report for International Application No. PCT/US2018/048177 mailed Dec. 20, 2018.

Khan et al., "Intentional Laceration of the Anterior Mitral Valve Leaflet to Prevent Left Ventricular Outflow Tract Obstruction During Transcatheter Mitral Valve Replacement", JACC: Cardiovascular Interventions vol. 9, No. 17, 2016.

Babaliaros et al., "Intentional Percutaneous Laceration of the Anterior Mitral Leaflet to Prevent Outflow Obstruction During Transcatheter Mitral Valve Replacement First-in-Human Experience", JACC: Cardiovascular Interventions vol. 10 , No. 8, 2017.

Lederman et al., "Preventing Coronary Obstruction During Transcatheter Aortic Valve Replacement From Computed Tomography to Basilica", JACC: Cardiovascular Interventions vol. 12 , No. 13. 2019, pp. 1197-1216.

Khan et al., "Predicting Left Ventricular Outflow Tract Obstruction Despite Anterior Mitral Leaflet Resection The "Skirt NeoLVOT"", JACC: Cardiovascular Interventions Sep. 2019, vol. 11 , No. 9, pp. 1356-1359.

Case, "Tip to Base Lampoon to PRevent Left Ventricular Outflow Tract Obstruction in Valve in Valve Transcatheter Mitral Valve Replacement", JACC: Cardiovascular Interventions, May 2020, vol. 13, No. 9, pp. 1126-1128.

Greenbaum et al., "First-in-human transcatheter pledglet-assisted suture tricuspid annuloplasty for severe tricuspid Insufficiency," Catheterization and Cardiovascular Interventions, May 2020, 5 pages.

Kamioka et al., "Bi-Silica During Transcatheter Aortic Valve Replacement for Noncalcific Aortic Insufficiency: Initial Human Experience", JACC: Cardiovascular Interventions, Nov. 2018, vol. 11, No. 21, pp. 2237-2239.

Kasel et al, "International Lampoon: First European experience with laceration of the anterior mitral valve leaflet prior to transseptal transcatheter mitral valve implantation", Eurointervention, Sep. 2018, col. 14, No. 7, pp. 746-749.

Khan et al, "The Basilica Trial: Prospective Multicenter Investigation of Intentional Leaflet Laceration to Prevent TAVR Coronary Obstruction", JACC: Cardiovascular Interventions, 2019, vol. 12, No. 13, pp. 1240-1252.

Khan et al, "Transcatheter Mitral Valve Replacement after Transcatheter Electrosurgical Laceration of Alfieri stitch (Elastic): First in human report," JACC: Cardiovascular Interventions, Apr. 2018, vol. 11, No. 8, pp. 1808-1811.

Khan et al, "Transcatheter Electrosurgery: JACC State of the art review," Journal of the American College of Cardiology, Mar. 2020, vol. 75, No. 12, pp. 1455-1470.

Khan et al., "Anterior Leaflet Laceration to Prevent Ventricular Outflow Tract Obstruction During Transcatheter Mitral Valve Replacement," Journal of the American College of Cardiology, May 2019, vol. 73, No. 20, pp. 2521-2534.

Khan et al, "Rescue Lampoon to Treat Transcatheter Mitral Valve Replacement—Associated Left Ventricular Outflow Tract Obstruction", JACC: Cardiovascular Interventions, Jul. 2019, vol. 12, No. 13, pp. 1283-1284.

(56) References Cited

OTHER PUBLICATIONS

Lisko et al., "Pachyderm Shape guiding catheters to simplify Basilica leaflet traversal," Cardiovsacular Revascularization Medicine, Sep. 2019, vol. 20, No. 9, pp. 782-785.
Lisko et al., "Electrosurgical detachment of Mitraclips from the anterior mitral leaflet prior to transcatheter mitral valve implantation," JACC: Cardiovascular Interventions, Oct. 2020, vol. 13, No. 20, pp. 2361-2370.
Khan et al., "Lampoon to facilitate tendyn Anterior Leaflet Laceration to Prevent Ventricular Outflow Tract Obstruction During Transcatehter Mitral Valve Replacement," Journal of the American College of Cardiology, May 2019, vol. 73, No. 20, pp. 2521-2534.
Written Opinion and International Search Report mailed Mar. 1, 2021 for International Patent Application No. PCT/US2020/055160.
Written Opinion mailed Jan. 27, 2022 for International Patent Application No. PCT/US2021/049952.
International Search Report mailed Jan. 27, 2022 for International Patent Application No. PCT/US2021/049952.
Unpublished International Patent Application No. PCT/US2021/049952 downloaded from ePCT on Jan. 28, 2022.
Supplementary European Search Report and European Search Opinion for Application No. 19756527.8 dated Oct. 18, 2021.
Written Opinion and International Search Report mailed Oct. 22, 2021 for International Patent Application No. PCT/US2021/040511.
Extended European Search Report for Application No. 18848165.9 dated Apr. 30, 2021.

* cited by examiner

CATHETERS AND MANIPULATORS WITH ARTICULABLE ENDS

CROSS-REFERENCE TO RELATED APPLICATIONS

This patent application is a continuation-in-part of and claims the benefit of priority to International Patent Application No. PCT/US2018/48177, filed Aug. 27, 2018, which in turn claims the benefit of priority to U.S. Provisional Application Ser. No. 62/550,347, filed Aug. 25, 2017, U.S. Provisional Application Ser. No. 62/567,203, filed Oct. 2, 2017, U.S. Provisional Patent Application Ser. No. 62/663,518, filed Apr. 27, 2018, U.S. Provisional Application Ser. No. 62/688,378, filed Jun. 21, 2018, and U.S. Provisional Patent Application Ser. No. 62/712,194, filed Jul. 30, 2018. The present application also claims the benefit of priority to U.S. Patent Application Ser. No. 62/728,413, filed Sep. 7, 2018. Each of the foregoing patent applications is incorporated by reference herein in its entirety for any purpose whatsoever.

BACKGROUND

The disclosure relates generally to medical treatment devices and techniques, and, in some aspects, to methods and devices for diagnosis and treatment of cardiac valves. The present disclosure provides improvements over the state of the art.

SUMMARY OF THE DISCLOSURE

The present disclosure provides various systems and methods for removing clips, cysts and other structures from valve leaflets. The disclosure further provides systems for modifying or removing luminal valve leaflets. The disclosure also provides other innovations, as set forth below.

DETAILED DESCRIPTION

The present disclosure provides a variety of methods and systems. In some implementations, the disclosure provides systems and methods to remove structures that are no longer desired in the anatomy. For example, if an Alfieri stitch, or a clip, is used to attach a portion of two cardiac leaflets to each other, the disclosed embodiments can be used to cut through one or both of the leaflets to free them from each other, and to also prepare the site, if desired, for a replacement valve, such as by forming one or more additional cuts in each native leaflet, and/or removing a portion of, or substantially the entirety of, or the entirety of, one or more of the native leaflets. If desired, all the leaflets can be removed, and any structures attached thereto (e.g., chordae) can also be cut and/or removed. In some implementations, a suture or clip (e.g., a MitralClip) can be removed from a patient's mitral valve, after which further therapeutic steps can be performed including repair of the valve leaflets, reshaping of the valve leaflets, removing all or a portion of one or all leaflets, or cutting the leaflets and any chordae out of the way, as desired, to make room for a replacement valve.

Similar procedures for resecting or cutting tissue anywhere in the body can be used by utilizing devices and methods in accordance with the present disclosure. Such procedures can be used for cutting valve leaflets, for example, in any of the cardiac valves, any valves in veins, such as the IVC, or for cutting any other anatomical structures in the body.

Any suitable power level and duty cycle can be used in accordance with the disclosed embodiments when electrified tissue cutting techniques are used. For example, continuous duty cycle (cutting) radiofrequency ("RF") energy can be used, for example, at a power level between about 50 and 100 Watts, or any increment therebetween of about one watt. The cuts can be made by applying power for between about one half of a second and about five seconds, or any increment therebetween of about one tenth of a second.

Figure 1:
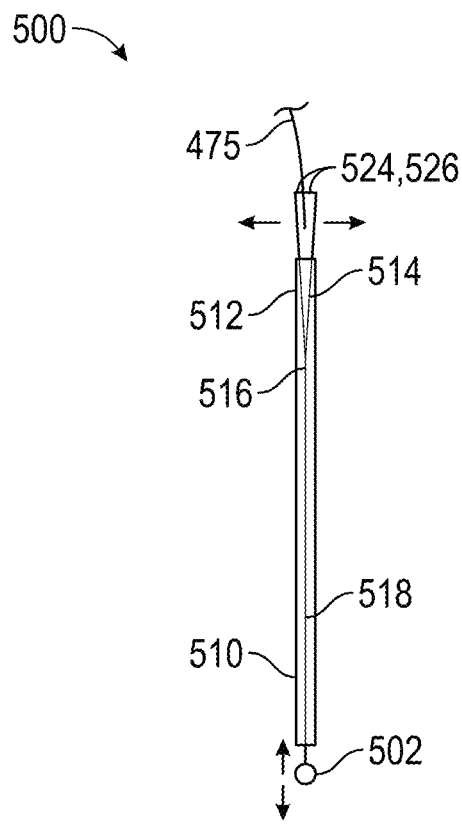
FIG. 1 presents a further embodiment of a grasping catheter in accordance with the present disclosure.

FIG. 1 presents an alternative embodiment of a grasping catheter 500 that can be used in place of a pair of catheters simply for grasping the edge of a leaflet 475. The catheter 500 includes a tubular outer body 510 having a proximal end, a distal end and a longitudinal passage therethrough. An internal slidable gripping mechanism is slidably disposed within the lumen of outer body 510 that includes a proximal actuator or handle 502 that is connected to an elongate inner body 518 that separates at a bifurcation 516 into a first arm 512 and a second arm 514, that in turn terminate in inwardly pointed gripping ends 524, 526. Arms 512, 514 are biased away from each other, and can be urged together by withdrawing the arms and accompanying tips toward the distal end of the tubular member 510. Accordingly, by controlling the relative placement of the inner mechanism and outer tube, the jaws formed by arms 512, 514 and gripping ends 524, 526 can be opened and closed. Catheter 500 can be used as a sub-catheter in any embodiment herein.

The disclosure also provides a robotic manipulator having a proximal end and a distal end that includes an elongate tubular arm having a proximal end, a distal end, and defining at least one elongate passage therethrough, the elongate tubular arm defining a longitudinal axis along its length. The manipulator further includes a first elongate inner body having a proximal end and a distal end that is slidably disposed within the at least one elongate passage of the elongate tubular arm, the distal end of the first inner elongate body being biased (or otherwise configured, such as preforming and/or steering wire) to curl away from the longitudinal axis in a proximal direction when the first elongate inner body is advanced distally with respect to the arm. The manipulator can further include a second elongate inner body having a proximal end and a distal end that is slidably disposed within the at least one elongate passage of the elongate tubular arm that can be slidably disposed with respect to the first inner body. The distal end of the second inner elongate body can be biased to curl away from the longitudinal axis toward the deployed proximally oriented distal end of the first elongate inner body when the second elongate inner body is advanced distally with respect to the arm.

At least one of the elongate tubular arm, first elongate inner body or second elongate inner body can be connected to an axial actuator, wherein the actuator is configured to advance the component to which it is connected along a direction parallel to the longitudinal axis. Moreover, at least one of the elongate tubular arm first elongate inner body or second elongate inner body can be connected to a rotational actuator, wherein the rotational actuator is configured to rotate one or more of the elongate tubular arms, first elongate inner body and second elongate inner body.

At least one of the first elongate inner body and second elongate inner body can include an end effector attached thereto configured to perform at least one of a cutting, grasping, irrigating, evacuating, viewing or suctioning function. If desired, the end effector can include one or more of an electrosurgical device, a blade, and an ultrasonic transducer.

The disclosure also provides implementations of a laparoscopic, urinary, gynecological, neurological, or orthopedic surgical procedure utilizing the catheters or robotic manipulators disclosed herein. The disclosed catheters/manipulators can also be used in any suitable minimally invasive procedure, or a percutaneous procedure.

For example, the percutaneous procedure can include utilizing one or more of the disclosed devices to access a patient's sinus passages. The devices can be used, for example, to remove one or more polyps, and can even be used to breach a thin bony layer within the sinuses to access the cranial cavity to perform a procedure inside the cranial cavity.

In other embodiments, the percutaneous procedures disclosed herein can include an ablation procedure, such as within the heart of a patient or elsewhere, as well as a cryoablation procedure.

Figure 2:
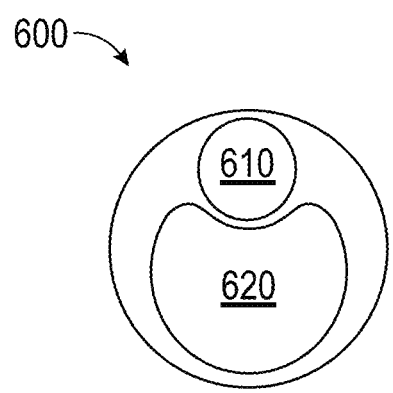
FIG. 2 illustrates a cross sectional view of an extruded main body portion of an illustrative catheter in accordance with the disclosure.

In further accordance with the present disclosure, FIG. 2 illustrates a cross sectional view of an extruded main body portion 600 of a further embodiment of a catheter. The body includes an extrusion defining two offset channels 610, 620. A first channel 610 is illustrated as having a generally circular cross-section, and the second channel 620 that is parallel thereto is illustrated as having a cross-section that is circular with a scalloped portion removed in order to accommodate the channel with the circular cross section. The main body 600 can be made from any suitable polymeric material, such as those set forth herein. The main body can be formed from a multilayer polymeric extrusion with one or more reinforcement (e.g. layers of braiding) formed thereon or therein. The main body can be coated with any suitable coating or material to enhance its lubricity, as desired.

Figure 3A:
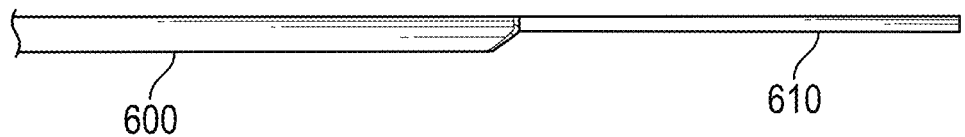
FIGS. 3A-3D present various embodiments of a dual lumen catheter in accordance with the present disclosure.
Figure 3B:
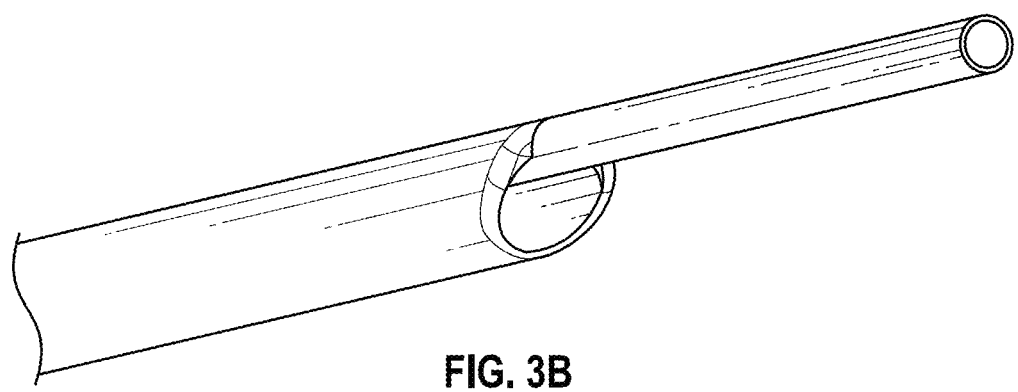

FIG. 3A presents a side view of the illustrative catheter of FIG. 2 including the main shaft 600 described above, provided with at least one braided layer. The catheter further includes a distal tubular segment extending distally from main shaft 600 that defines therein lumen 610 that is radially co-located with the first channel of the main body. For example, the distal tubular segment can be an extruded tube that extends the full length along the inside of the main body to a proximal end of the catheter. The distal tubular segment may similarly be braided if desired, may be pre-curved as described elsewhere herein and/or can be deflectable, for example, by providing a pull wire within the lumen of the distal segment, or within a co-extruded lumen of the distal segment (not specifically illustrated). A distal end of the pull wire (not shown) can be attached to a collar embedded within or on the distal tubular segment, as desired. As illustrated in FIG. 3B, the distal tubular segment and its associated channel that it surrounds can be used to act as a guidewire lumen, permitting the catheter to be used as an over the wire catheter, or for delivering a lower profile catheter therethrough, such as a snare catheter, as set forth in further detail below.

Figure 3C:
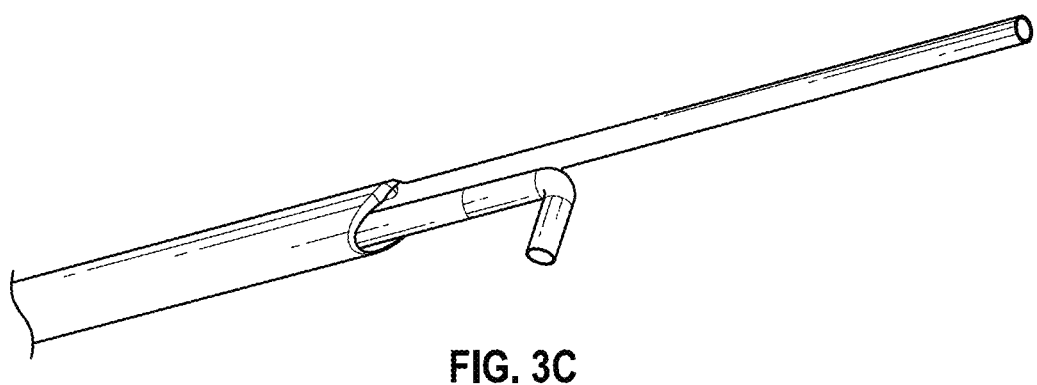
Figure 3D:
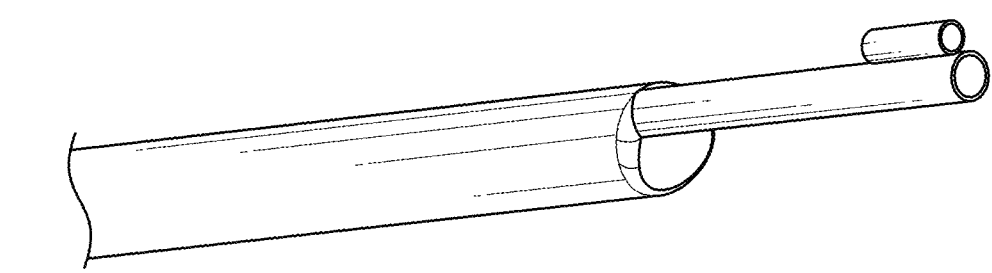

FIG. 3C illustrates an embodiment wherein the larger/major, e.g., non-circular, lumen defined in the main body can act as a delivery lumen for a catheter that can be steerable (e.g., by a steering wire) or that can have a curve preformed into it (e.g., by heating and bending the catheter if polymeric in composition) that the catheter can assume after it is advanced distally out of the distal end of the major lumen of the main body. As presented in FIG. 3D, the distal tubular segment can be provided with a further tubular member disposed thereon, or integrated therewith in a co-extrusion, that can act as a guidewire lumen to facilitate a rapid exchange ("RX") procedure with the guidewire rather than having the guidewire traverse the entire length of the catheter as in an over the wire ("OTW") procedure.

Figure 4:
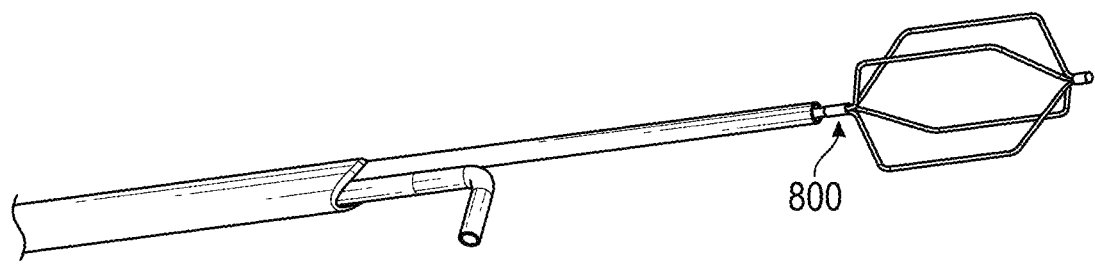
FIG. 4 presents the embodiment of FIG. 3A including a snare catheter disposed through the minor lumen for effectuating capture, for example, of a guidewire in a medical procedure.

FIG. 4 presents the embodiment of FIGS. 3A-3D, but including a snare catheter 800 disposed through the minor lumen for effectuating capture, for example, of a guidewire in a mitral cerclage procedure as set forth in U.S. patent application Ser. No. 15/796,344, filed Oct. 27, 2017. Further aspects of the snare catheter can be seen in that application, as well as in U.S. Provisional Patent Application Ser. No. 62/615,309, filed Jan. 9, 2018. Each of the foregoing applications is hereby incorporated by reference for any purpose whatsoever. The present catheter can be used, for example, for such mitral cerclage procedures. For example, the snare catheter can be used to capture a guidewire while the major passage accommodates an articulating catheter as described hereinabove for grasping a cardiac valve leaflet, or other structure.

Figure 5A:
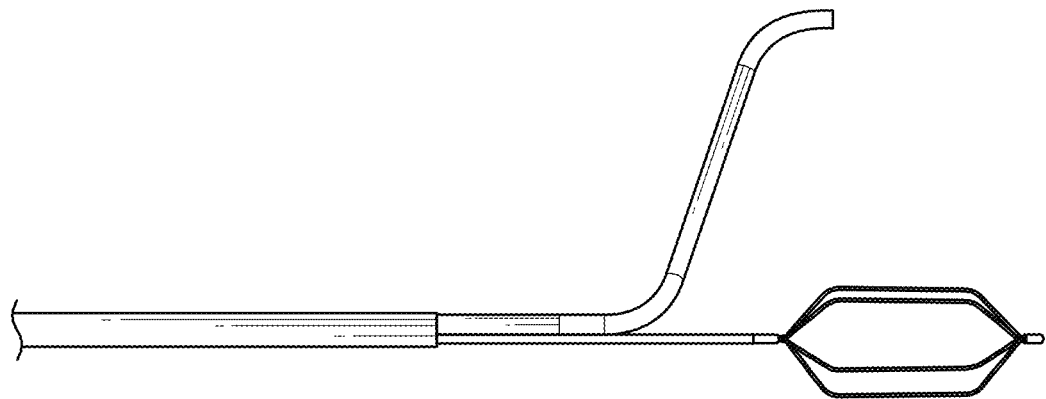
FIGS. 5A-5B illustrate an articulating catheter having two preformed bends that resume their bent shape when advanced distally from the main catheter.
Figure 5B:
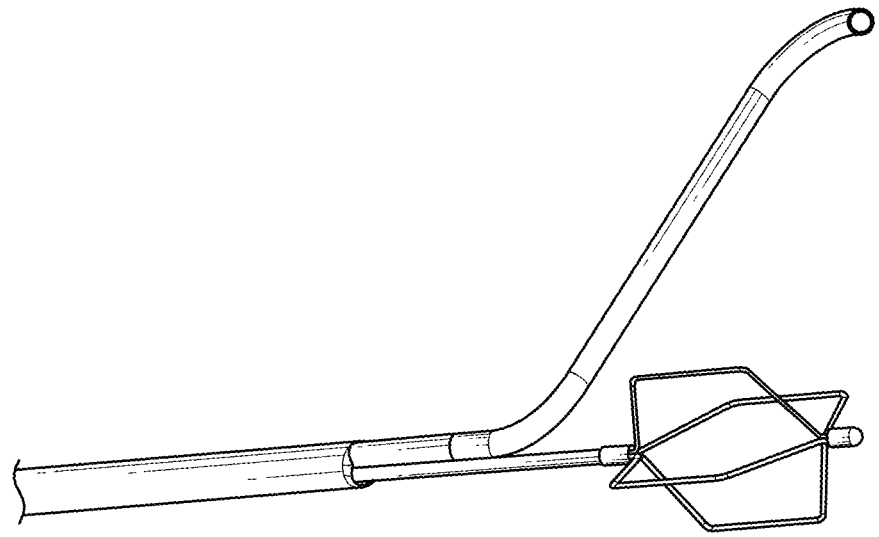
Figure 6:
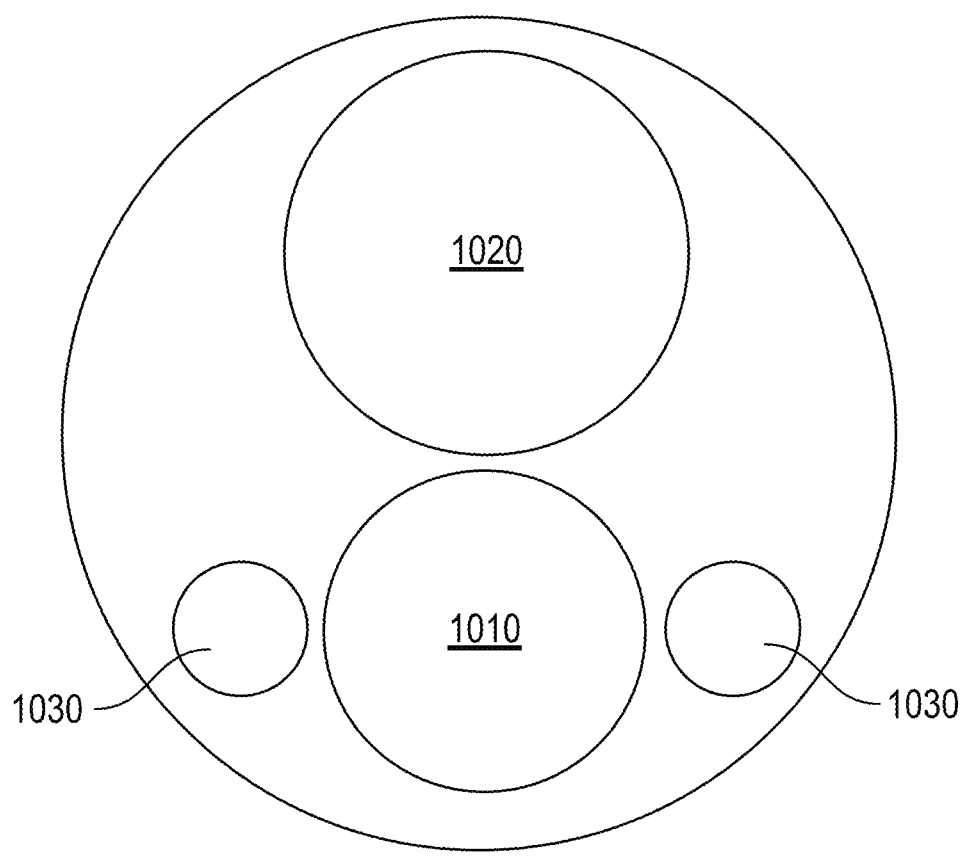
FIG. 6 illustrates an illustrative cross section of a catheter in accordance with the present disclosure.

A further embodiment is presented in FIGS. 5A-5B, which illustrates an articulating catheter having two pre-formed bends that resume their bent shape when advanced distally from the main catheter. FIG. 6 illustrates a further possible cross section for the main catheter, wherein major and minor lumens 1010, 1020 are presented, but two additional steering wire lumens 1030 are presented. If desired, further steering wire lumens are presented that can be used for housing a pull wire that is attached at its distal end to a portion of the catheter (not shown), such as to a ring collar that is formed on or in the body of the catheter.

Figure 7A:
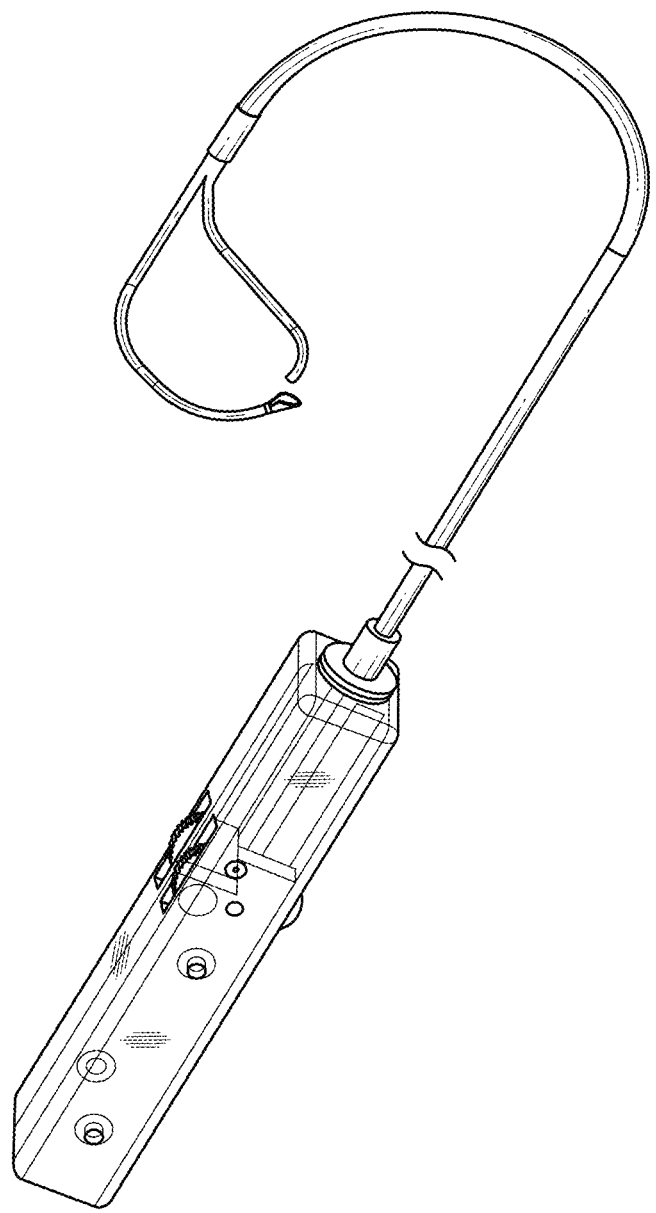
FIGS. 7A-7C present various views of a further embodiment of a catheter in accordance with the present disclosure.
Figure 7B:
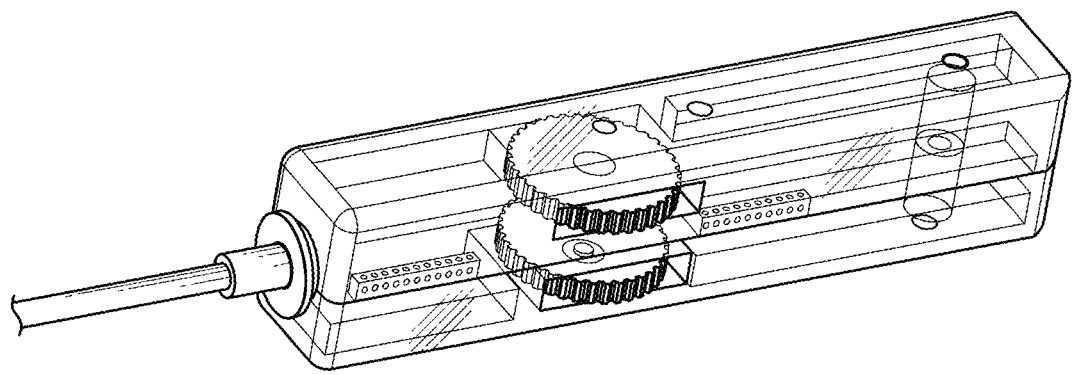
Figure 7C:
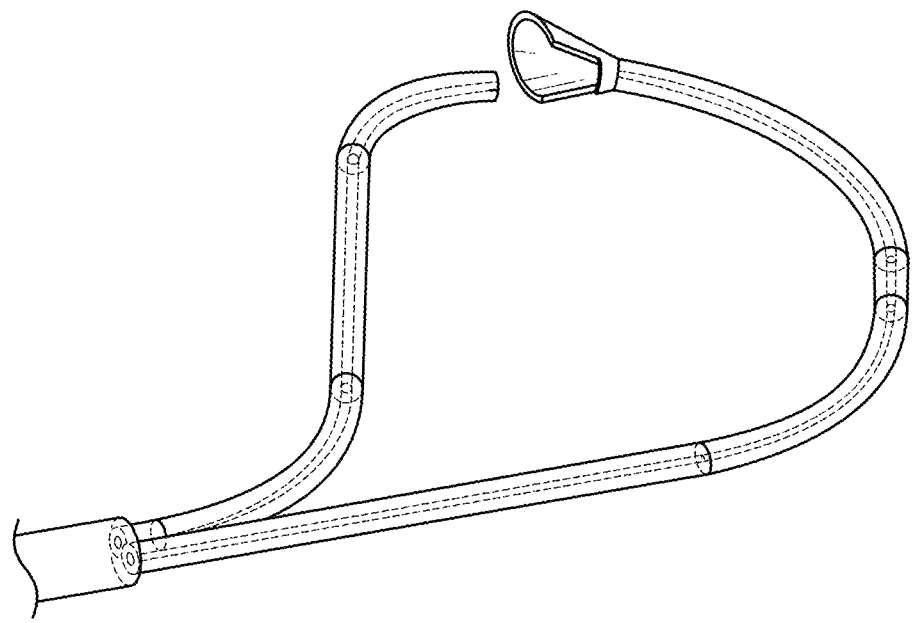
Figure 8A:
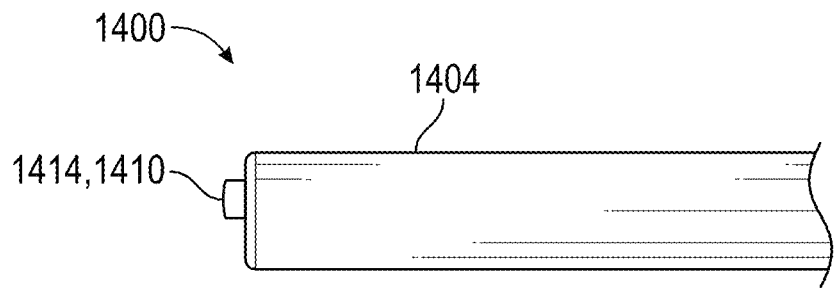
FIGS. 8A-8E present views of still a further catheter in accordance with the present disclosure.
Figure 8B:
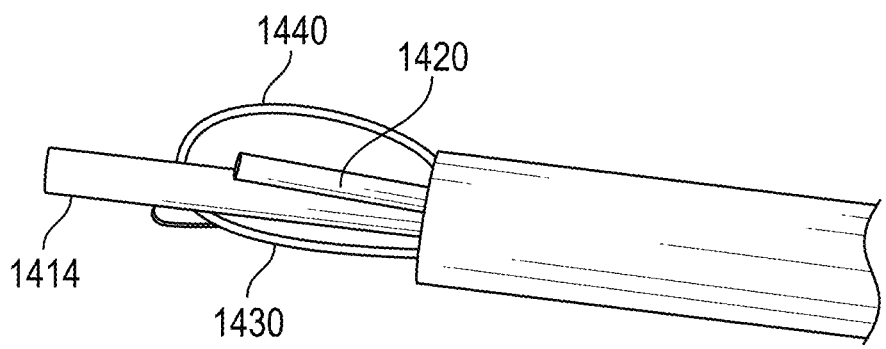
Figure 8C:
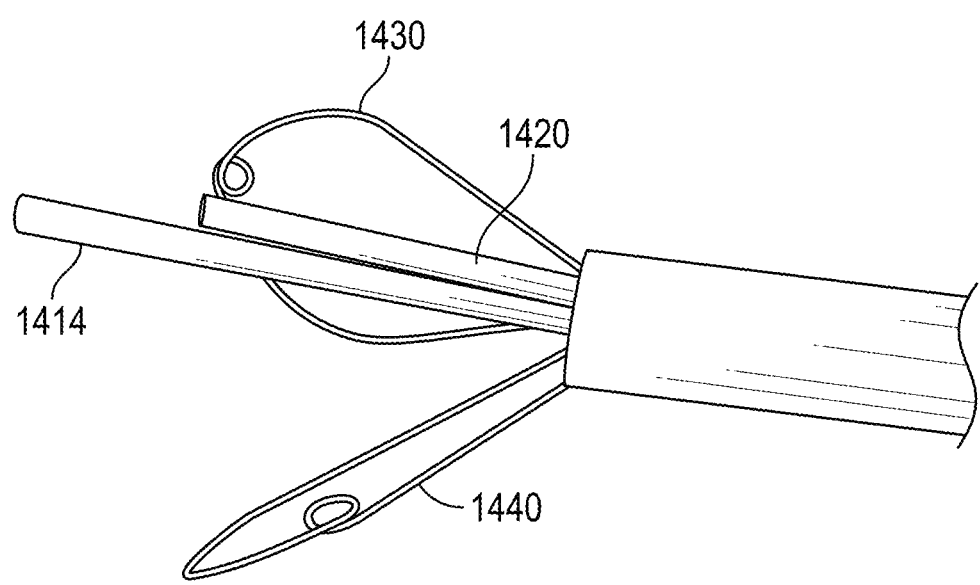
Figure 8D:
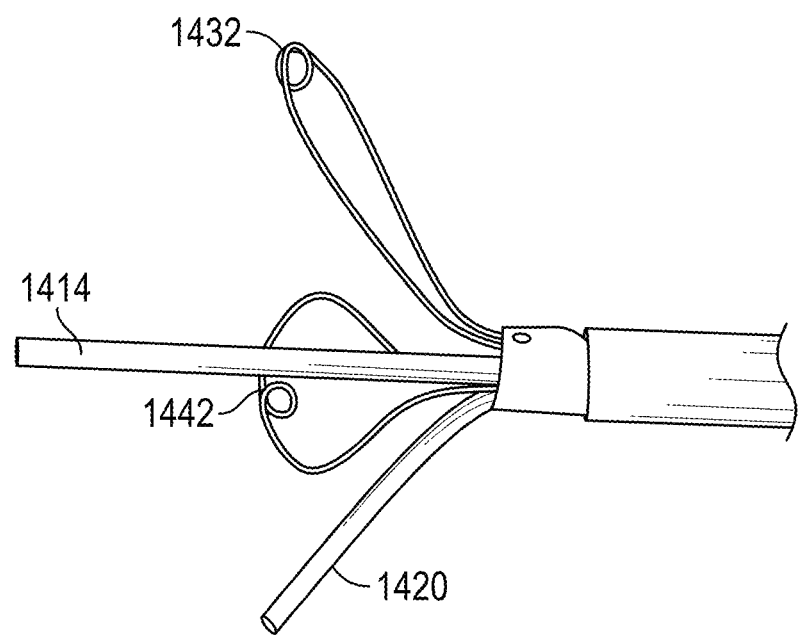
Figure 8E:
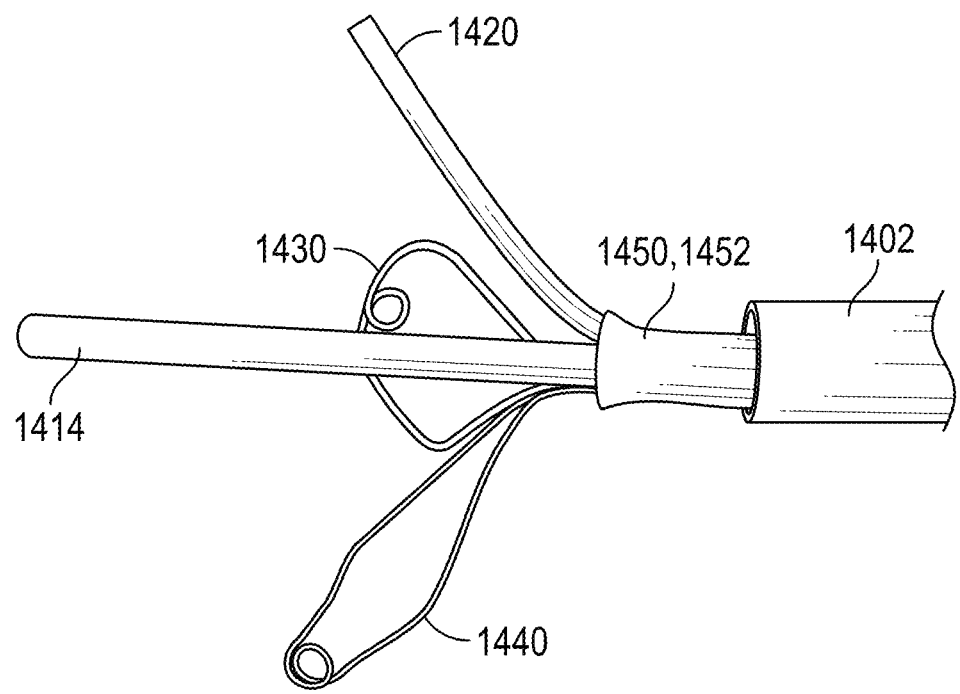

FIGS. 7A-7C display a further embodiment of a catheter in accordance with the disclosure (or aspects thereof) that includes a scoop on one of the articulating arms as presented. The scoop, or funnel, can help guide the other articulating arm into contact with it. If desired, permanent magnets can be added at the end of each articulating arm (not shown), or a winding around each end of the catheter can be made to form a solenoid on the end of each of the arms (not shown). When electrical current is run along the same helical direction through each solenoid, the created magnetic fields add to each other, and attract each other, causing the arms to move more closely together into contact. The force is directly proportional to the current that passes through the windings. Also illustrated is a push-pull actuator for relatively articulating each of the deployable limbs in the catheter. The disclosed catheter uses a toothed wheel, or gear, that rotates around an axle and engages a gear rack in a sliding track that in turn is attached to one of the articulating arms.

For purposes of illustration, and not limitation, FIGS. 8A-9C depict yet another embodiment of a catheter in accordance with the present disclosure.

FIGS. 8A-8E illustrate a further embodiment 1400 of a catheter. The distal end 1404 of catheter 1400 is depicted to highlight its functionality. Catheter 1400 also includes a proximal end and elongate body (not shown) having one or more actuators to manipulate the various sub-components of catheter 1400 described in detail below. Catheter 1400 is defined by an outer tubular member having a proximal end, a distal end 1404, and defines an elongate passage therethrough along its length. Elongate passage slidably accommodates an intermediate tubular member 1450 therein having a proximal end (not shown), a distal end 1452 and in turn also defining a passage along its length for slidably receiving a subassembly therein including at least one further catheter, tool or manipulator. As illustrated in FIGS. 8A-8E, a subassembly is provided slidably received within intermediate tubular member 1450 that includes a central tubular member 1410 having a proximal end, a distal end 1414, and defining a passage along its length, for example, for receiving a guidewire for guiding catheter 1400 to a target location. As illustrated, central tubular member 1410 is a straight member, but can be imparted with a curvature if desired. The subassembly further includes a second tubular member 1420 having a proximal end (not shown), a distal end 1424 and an elongate body defining a central lumen along its length. Second tubular member 1420, as illustrated, has a curvature imparted to it. Also provided are collapsible loops 1430, 1440, which may be made from any suitable material. The particular loops illustrated are formed from nitinol. Each loop is defined by a filament that can include a stress distribution loop (1432, 1442) formed therein that traverses 360 degrees or more. Providing a stress distribution loop facilitates collapse of the loops 1430, 1440 by distributing the bending stress over a longer effective length of wire. The material from which loops 1430, 1440 is formed can extend to the proximal end of the catheter 1400, or may be secured in the distal ends of additional tubular members (not shown) that are slidably disposed in intermediate tubular member 1450. Loops can be made, for example, from shape memory material such as various nickel titanium alloys.

As illustrated, the subassembly within tubular member 1450 can be both slidably and rotatably movable with respect to the outer tubular member of catheter 1400. If desired, each of the subcomponents 1410, 1420, 1430 and 1440 may be slidably and rotatably movable with respect to each other, and the main body of the catheter 1400 as well as the intermediate tubular member 1450.

Figure 9A:
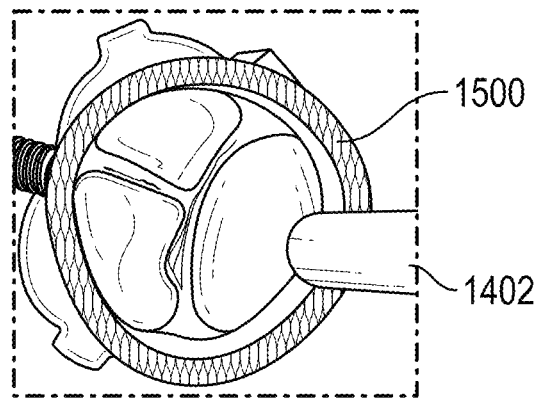
FIGS. 9A-9C present views of a procedure using the embodiment of FIGS. 8A-8E with respect to the anatomical structure of a tricuspid valve.
Figure 9B:
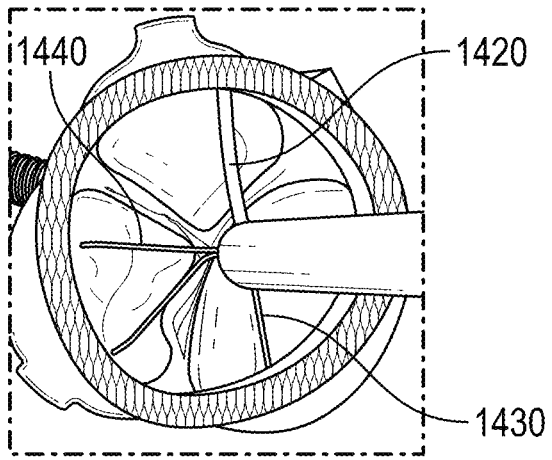
Figure 9C:
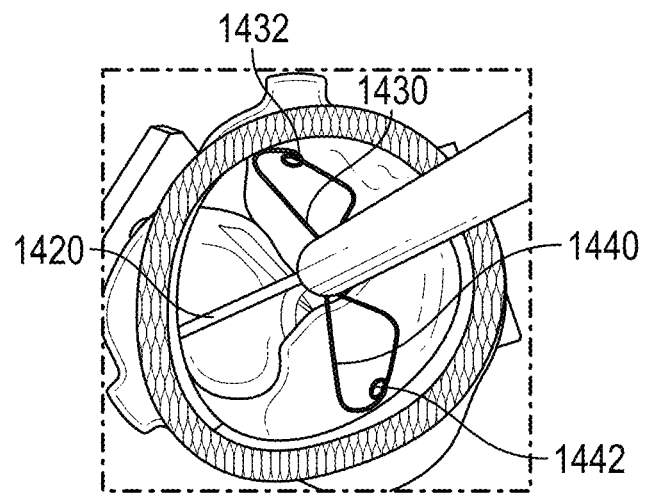

As illustrated in FIGS. 9A-9C, the embodiment 1400 is illustrated in use with respect to the structure of a tricuspid valve. In use, after the distal end 1402 of catheter 1400 is advanced, for example, to a tricuspid valve, the subassembly housed within intermediate tubular member 1450 is advanced distally out of distal end 1402 of catheter 1400, and the distal end 1414 of central tubular member 1410 can be directed through the center of the tricuspid valve between the leaflets. Next, the two loops 1430, 1440 are deployed and advanced under the leaflet against the center of each leaflet by the valve annulus. This permits tubular member 1420 to be positioned at the center of the third leaflet by the annulus. At this time, any desired instrument, such as a cutting wire or piercing instrument can be advanced through the leaflet at its edge by the annulus, such as to advance an electrosurgical cutting wire through the leaflet, permitting the cutting wire to be dragged radially inwardly through the leaflet to cut the leaflet in half. In accordance with a further example, a suture can be anchored by subassembly component 1420. The suture can then be used as a guide rail for delivering a prosthesis to be implanted over the leaflet, without cutting it in half first. It will be appreciated that catheter 1400 can be used in many different types of procedures and that these illustrations are only examples.

The devices and methods disclosed herein can be used for other procedures in an as-is condition, or can be modified as needed to suit the particular procedure. In view of the many possible embodiments to which the principles of this disclosure may be applied, it should be recognized that the illustrated embodiments are only preferred examples of the disclosure and should not be taken as limiting the scope of the disclosure. Each and every patent and patent application referenced herein is expressly incorporated by reference herein in its entirety for any purpose whatsoever.

What is claimed is:

1. A method of removing cardiac valve tissue, comprising:
providing a tissue dissection and removal catheter, the tissue dissection and removal catheter having a proximal end, a distal end and defining a longitudinal axis along its length, the tissue dissection and removal catheter including:
an outer tubular member having a proximal end, a distal end, and defining an elongate passage therethrough along its length; and
a subassembly slidably disposed in the elongate passage of the outer tubular member, the subassembly including first and second deployable stabilizers, the first and second deployable stabilizers each being configured to expand in lateral width along a direction transverse to the longitudinal axis when unconstrained by the outer tubular member, each said stabilizer defining a curved free distal end that is being configured to be received within a cusp of a respective cardiac valve leaflet, wherein the curved free distal end of each said stabilizer faces along a distal direction such that distal advancement of the subassembly urges the curved free distal end of each stabilizer into a respective cardiac valve cusp;
introducing the tissue dissection and removal catheter into a patient at a target location within a patient's vasculature;
advancing the subassembly along a distal direction toward an underside of a cardiac valve;
individually deploying the first and second deployable stabilizers out of the outer tubular member;
directing the curved free distal end of each said stabilizer into respective first and second cusps of the cardiac valve adjacent a circumferential wall surrounding the cardiac valve to stabilize the position of the valve leaflet dissection and removal catheter with respect to the target location, wherein each said deployable stabilizer stabilizes the subassembly in place without individually grasping cardiac tissue, and further wherein the first and second deployable stabilizers are configured to be slidably and rotatably articulable with respect to each other;
deploying a further tool out of the outer tubular member, the further tool being slidably and rotatably displaceable with respect to the first and second deployable stabilizers; and removing tissue from the cardiac valve at least in part by using the further tool.

2. The method of claim 1, wherein tissue that is removed using the further tool is attached to a stitch, wherein the stitch joins at least two native valve leaflets together, and further wherein the tissue removing step results in the at least two native valve leaflets becoming separated from each other.

3. The method of claim 2, wherein tissue that is removed using the further tool is coupled to a valve leaflet clip, wherein the valve leaflet clip joins at least two native valve leaflets together, and further wherein the tissue removing step results in the at least two native valve leaflets becoming separated from each other.

4. The method of claim 3, wherein the tissue that is removed using the further tool is removed with the valve leaflet clip.

5. The method of claim 1, further comprising removing at least a portion of a valve leaflet from an adjacent structure.

6. The method of claim 5, wherein substantially the entirety of at least one valve leaflet is removed.

7. The method of claim 5, wherein the entirety of at least one valve leaflet is removed.

8. The method of claim 5, wherein all the leaflets of a valve at the target location are removed.

9. The method of claim 8, wherein structures coupled to the valve are cut or removed.

10. The method of claim 8, wherein valve chordae are cut or removed.

11. The method of claim 1, wherein each of the stabilizers includes a self-expanding loop of material that expands radially outwardly and laterally outwardly.

12. The method of claim 11, wherein at least one of the stabilizers is formed from a loop of shape memory material.

13. The method of claim 12, wherein at least one of the stabilizers includes a first length of material and a second length of material, each said first length of material and second length of material including a respective proximal end attached to the subassembly, each said first and second lengths of material further including a respective distal end attached to opposing ends of a 360 degree loop of material, wherein the 360 degree loop of material facilitates lateral collapsing and deployment of said at least one of the stabilizers, and further wherein said 360 degree loop of material is located at a midpoint of the curved free distal end of said at least one of the stabilizers.

14. The method of claim 1, wherein the first and second deployable stabilizers are formed from a nickel titanium alloy.

15. The method of claim 1, further comprising moving the subassembly both slidably and rotatably with respect to the outer tubular member to align the first and second deployable stabilizers with respect to surrounding anatomy.

\* \* \* \* \*